United States Patent
Peterson et al.

(10) Patent No.: US 9,310,309 B1
(45) Date of Patent: Apr. 12, 2016

(54) METHOD OF SENSING ACIDIC/ACID-FORMING AND OXIDIZABLE GASES FOR USE AS A RESIDUAL FILTER LIFE INDICATOR

(71) Applicant: U.S. Army Edgewood Chemical and Biological Command, Washington, DC (US)

(72) Inventors: Gregory W. Peterson, Belcamp, MD (US); James E Whitten, Hudson, NH (US); Evan J. Watters, North Billerica, MA (US)

(73) Assignee: The United States of America, as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/134,413

(22) Filed: Dec. 19, 2013

Related U.S. Application Data

(60) Provisional application No. 61/767,504, filed on Feb. 21, 2013.

(51) Int. Cl.
| | |
|---|---|
| *A62D 3/30* | (2007.01) |
| *A62D 3/00* | (2007.01) |
| *G01N 21/17* | (2006.01) |
| *G01N 21/64* | (2006.01) |
| *G01N 21/76* | (2006.01) |

(52) U.S. Cl.
CPC ...................................... *G01N 21/76* (2013.01)

(58) Field of Classification Search
CPC ............. A62D 3/36; A62D 3/30; A62D 3/00; Y10T 436/00; Y10T 436/11; G01N 21/17; G01N 21/00; G01N 21/1748; G01N 21/64; G01N 21/62; G01N 21/625; G01N 21/6489
USPC .......................................... 436/117, 116, 106
See application file for complete search history.

(56) References Cited

U.S. PATENT DOCUMENTS

2013/0040150 A1 *  2/2013  Trexler et al. .............. 428/425.9

FOREIGN PATENT DOCUMENTS

WO   WO 2006/119986   * 11/2006 ............. G01N 33/00

OTHER PUBLICATIONS

Singh J. et al, Sulfur dioxide and nitrogen dioxide adsorption on zinc oxide and zirconium hydroxide nanoparticles and the effect on photoluminescence, Applied Surface Science, Feb. 24, 2012, 258, pp. 5778-5785.*
Peterson, Gregory et al, Removal of Chlorine Gases from Streams of Air Using Reactive Zirconium Hydroxide Based Filtration Media, Industrial & Engineering Chemistry Research, 2012, 51, pp. 2675-2681.*
Whitten, James E., Surface Chemistry Studies Related to Residual Life Indicators, Mar. 2011, U.S. Army Research Office, pp. 1-11.*

* cited by examiner

*Primary Examiner* — Christine T Mui
(74) *Attorney, Agent, or Firm* — Ulysses John Biffoni

(57) ABSTRACT

Processes of detecting the presence of an environmental challenge such as contact with an acidic/acid-forming and/or oxidizable gas are provided whereby a metal oxyhydroxide is used as a detection agent. The metal oxyhydroxide will irreversibly interact with an acidic/acid-forming and/or oxidizable gas causing a red-stretch of the emission spectra. This red-stretch alters the ratio of emission intensities at higher wavelengths relative to lower wavelengths. A reduced post-exposure photoluminescence ratio is, therefore, used to detect exposure to such a gas or environmental challenge. The materials and processes may be used as a residual life indicator for filtration systems or for the detection of environmental challenges.

26 Claims, 5 Drawing Sheets

METHOD OF SENSING ACIDIC/ACID-FORMING AND OXIDIZABLE GASES FOR USE AS A RESIDUAL FILTER LIFE INDICATOR

GOVERNMENT INTEREST

The invention described herein may be manufactured, used, and licensed by or for the United States Government.

RELATED APPLICATIONS

This application claims the benefit of priority from U.S. Provisional Application Ser. No. 61/767,504 filed on Feb. 21, 2013.

FIELD OF THE INVENTION

The invention relates to methods and devices that may be used to monitor the presence or absence of a chemical in the environment. More specifically, methods are provided for quantifying the amount of an oxidizable gas. The methods and devices provided by the invention may be used in respirators and/or collective protection filters for use as end-of-service life indicators (ESLI) and/or residual life indicators (RLI). Devices employing the invention alert a user to when it is time to change-out the filter.

BACKGROUND OF THE INVENTION

Air purification, including individual and collective protection filtration, is of major concern to the military, first responders, and industrial workers. Filters typically containing activated, impregnated carbons are employed to filter toxic chemicals, and have limited lifetimes after exposure. Furthermore, due to interaction with environmental contaminants, such as SOx, NOx, hydrocarbon vapors, etc., the capacity of filters can degrade even before a toxic chemical event.

In individual protection having an end-of-service-life indicator (ESLI) that tells the user when the filter has run out of protective capability is a major development thrust, and a need for the community. Here, an ESLI should interact/react with toxic chemicals such that a response (ideally visible, but not necessarily) occurs. There are ESLI technologies currently being fielded; however, there are severe shortcomings to these, such as poor sensing of reactive gases or insufficient reactivity.

Due to continuous operation of filtration devices, ambient and battlefield contaminants (BFCs) decrease physical adsorption and chemical reactivity of the filter material over time due to interactions with the pore structure or the impregnants associated with the filter material contained within the filter housing. Residual life indicator (RLI) technologies have been developed; however, most do not accurately determine the effects of acidic/acid-forming contaminants on residual life.

As such, new processes are needed for the detection and quantification of acidic/acid-forming contaminants that may be employed to determine the residual life of a filtration system.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The present invention describes processes for sensing a variety of toxic chemicals and/or ambient contaminants, processes for determining the residual life of a filter or filtration system, and processes for determining the quality of manufactured metal oxyhydroxides.

Process for sensing an acidic/acid-forming and/or oxidizable gas include: contacting an acidic/acid-forming and/or oxidizable gas with a metal oxyhydroxide for a sampling time; obtaining a post-exposure photoluminescence of said metal oxyhydroxide; determining a difference between the post-exposure photoluminescence and a pre-exposure photoluminescence or control; and sensing the acidic/acid-forming and/or oxidizable gas by the presence of difference between the post-exposure photoluminescence and a pre-exposure photoluminescence or control. The process is capable of detecting an acidic/acid-forming and/or oxidizable gas by measuring a photoluminescence difference resulting from the gas directly reacting with a surface of said metal oxyhydroxide. In some embodiments, the acidic/acid forming gas is sulfur dioxide, nitrogen dioxide, hydrogen chloride, or combinations thereof. Many different metal oxyhydroxides are operable optionally including those that include an alkali or transition metal. Optionally the metal oxyhydroxide is zirconium hydroxide, zinc oxyhydroxide, cobalt oxyhydroxide, or combinations thereof. The metal oxyhydroxide is optionally amorphous zirconium hydroxide. A metal oxyhydroxide optionally includes one or more fluorescent materials doped in or with the metal oxyhydroxide. Optional fluorescent materials include one or more lanthanides. In some embodiments, the post-exposure photoluminescence is a ratio of intensity of a first wavelength and a second wavelength. Optionally, the first wavelength is 418 nanometers and the second wavelength is 500 nanometers. The presence of an acidic/acid-forming and/or oxidizable gas is optionally detected when the post-exposure photoluminescence has a lower ratio than the pre-exposure photoluminescence. Some embodiments further include calculating a pre-exposure ratio of photoluminescence intensity at a first wavelength and a second wavelength; calculating a post exposure ratio of photoluminescence intensity at the first wavelength and the second wavelength; wherein the step of sensing is by calculating a difference between the pre-exposure ratio and the post-exposure ratio.

Also provided are processes of determining residual capacity of an in-service filter/filtration system including depositing one or more metal oxyhydroxides on a swatch of material or locating one or more metal oxyhydroxides within a filter material; optionally contacting an acidic/acid-forming and/or oxidizable gas with the metal oxyhydroxide for a sampling time or optionally contacting said metal hydroxide to heat for a sampling time; obtaining a post-exposure photoluminescence ratio of the metal oxyhydroxide between the photoluminescence intensity at a first wavelength and the photoluminescence intensity at a second wavelength; and determining the residual capacity by comparing the ratio to as pre-exposure ratio or control. Optionally the metal oxyhydroxide is zirconium hydroxide, zinc oxyhydroxide, cobalt oxyhydroxide, or combinations thereof. The metal oxyhydroxide is optionally amorphous zirconium hydroxide. A metal oxyhydroxide optionally includes one or more fluorescent materials doped in or with the metal oxyhydroxide. Optional fluorescent materials include one or more lanthanides. In some embodiments, the step of locating is by locating the metal oxyhydroxide in the filter material so as to be capable of tracking a wavefront of the acidic/acid-forming or oxidizable gas through said filter. Optionally, the metal oxyhydroxide is located in the filter distal from an exposure surface of the filter material. Some embodiments further include integrating a detector or portion thereof within the filter in electromagnetic contact with the metal oxyhydroxide.

Also provided are processes for the manufacture of a metal oxyhydroxide material including obtaining a post-manufacture photoluminescence of a metal oxyhydroxide material; determining a difference between the post-exposure photoluminescence and a control; and using or rejecting the use of a metal oxyhydroxide material, optionally in a filter, based on the difference. Optionally, a process further includes assembling a filter media, filter housing, or filtration system including the metal oxyhydroxide. Many different metal oxyhydroxides are operable optionally including those that include an alkali or transition metal. Optionally the metal oxyhydroxide is zirconium hydroxide, zinc oxyhydroxide, cobalt oxyhydroxide, or combinations thereof. The metal oxyhydroxide is optionally amorphous zirconium hydroxide. A metal oxyhydroxide optionally includes one or more fluorescent materials doped in or with the metal oxyhydroxide. Optional fluorescent materials include one or more lanthanides. In some embodiments, the post-exposure photoluminescence is a ratio of intensity of a first wavelength and a second wavelength. Optionally, the first wavelength is 418 nanometers and the second wavelength is 500 nanometers. The presence of an acidic/acid-forming and/or oxidizable gas is optionally detected when the post-exposure photoluminescence has a lower ratio than the pre-exposure photoluminescence. Some embodiments further include calculating a pre-exposure ratio of photoluminescence intensity at a first wavelength and a second wavelength; calculating a post exposure ratio of photoluminescence intensity at the first wavelength and the second wavelength; wherein the step of sensing is by calculating a difference between the pre-exposure ratio and the post-exposure ratio.

DETAILED DESCRIPTION OF EMBODIMENTS OF THE INVENTION

Figure 1:
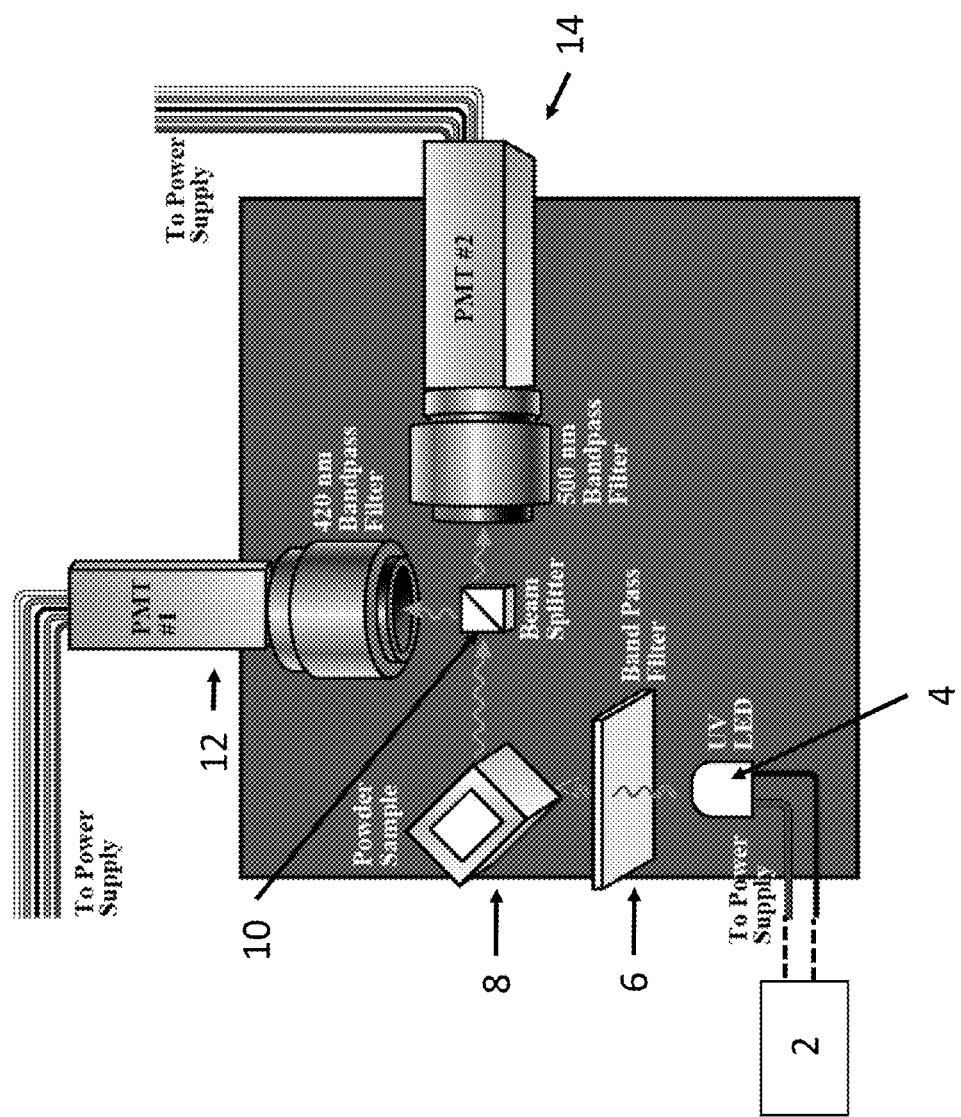
FIG. 1 is a schematic of an instrument useful in detecting a red-stretch from a metal oxyhydroxide according to an embodiment of the invention.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions are described as using specific materials in a particular order, it is appreciated that the described materials or order may be interchangeable such that the description of the invention includes multiple parts or steps arranged in many ways as is readily appreciated by one of skill in the art.

Ambient and battlefield contaminants such as sulfur dioxide, nitrogen dioxide, acid forming chemicals such as hydrogen chloride, and heavy organic vapors can detrimentally affect filter capacity for toxic chemicals. The present inventions provide processes and apparatuses that for the first time create a sensitive and robust response to these and similar chemicals to be useful to determine the residual capacity of in-service filters. Zirconium hydroxide has been developed for use in filters [1-5]. Initial investigations, however, were performed using crystalline zirconia ($ZrO_2$) as a metal oxyhydroxide, and not amorphous zirconium hydroxide ($Zr(OH)_4$) materials that have extremely different properties. In developing the processes of the present invention, the inventors performed initial studies analyzing crystalline zirconium hydroxide and zinc oxide photoluminescence (PL) before and after dosing with nitrogen dioxide and sulfur dioxide, among other chemicals. Processes are provided according to the present invention that build on these studies to create and detect changes in PL spectra before or after exposure and use these changes in PL spectra to detect and optionally quantify the amount of an environmental contaminant(s) producing the change in spectra.

A process is provided for sensing an acidic/acid-forming and/or oxidizable gas including optionally obtaining a pre-exposure photoluminescence of a metal oxyhydroxide, contacting an acidic/acid-forming and/or oxidizable gas with the metal oxyhydroxide for a sampling time, obtaining a post-exposure photoluminescence of a metal oxyhydroxide, and measuring a difference between the pre-exposure photoluminescence or control and the post-exposure photoluminescence. The process utilizes a peak shape change/expansion toward longer wavelengths (i.e., a "red stretch") in the PL spectra of a metal oxyhydroxide upon exposure to an acidic/acid-forming and/or oxidizable gas. Without being limited to one particular theory, it is believed that the red-stretch occurs as the result of an environmental challenge such as a chemical agent reacting with hydroxyl groups, possibly terminal hydroxyl groups, on the oxyhydroxide resulting in a stretch of the PL spectra intensity levels to longer wavelengths.

A process includes contacting an acidic/acid-forming and/or oxidizable gas with a metal oxyhydroxide for a sampling time. The contacting may be by active pressure combination optionally including mixing, by passive contact, or by other mechanism. The acidic/acid-forming and/or oxidizable gas is contacted to a metal oxyhydroxide for a sampling time. A sampling time may be any time from 0.1 seconds to 30 days or more, or any value or range between 0.1 seconds to 30 days. A sampling time is optionally 0.1 seconds to 24 hours, optionally 0.1 seconds to 1 hour, optionally 10 seconds to 20 minutes, optionally 1 minute to 20 minutes. A sampling time, in some embodiments, is any time sufficient to show a detectable stretch in PL intensity to a longer wavelength.

A process further includes obtaining a post-exposure photoluminescence of the metal oxyhydroxide and optionally a pre-exposure photoluminescence of the metal hydroxide. Measuring or determining the photoluminescence (PL) of a material is performed by one or more of many techniques known in the art. Illustratively, PL is determined using a fluorescence spectrometer, optionally a scanning fluorescence spectrometer, to determine fluorescence intensity of a metal oxyhydroxide at one or multiple wavelengths or ranges of wavelengths. Illustrative examples of such spectroscopic techniques can be found in Singh, J., et al., *Applied Surface Science*, 2012; 258:5778-5785. Illustratively, a metal oxyhydroxide is contacted by light of a desired wavelength from a first direction. Light emitted from the excited metal oxyhydroxide is detected from a second direction and the intensity of emitted light measured using one or more detectors. The relative intensity at one or more wavelengths changes, optionally increases, following contacting a metal oxyhydroxide with an acidic acid-forming and/or oxidizable gas or other environmental challenge. In some embodiments, the ratio of the intensity at a particular shorter wavelength to that at a particular longer wavelength decreases following a metal oxyhydroxide contacting an environmental challenge.

A red-stretch is optionally measured using a ratio of intensities at two wavelengths. For example, a post-exposure ratio is calculated by detecting the intensity of fluorescent light emitted from metal oxyhydroxide at a first wavelength and dividing the intensity of fluorescent light emitted from the metal oxyhydroxide at a second wavelength. A second wavelength is optionally longer than a first wavelength. A first wavelength is optionally at or near a peak fluorescence intensity. A first wavelength is optionally 418 nm+/−5 nm. A second wavelength is optionally 500 nm+/−5 nm. In some embodiments, a red stretch is detected by a higher intensity at optionally 500 nm relative to control or pre-exposure thereby correlating to a lower intensity ratio of first wavelength to second wavelength. In some embodiments, a red stretch is quantified or detected by measuring an increase in the photoluminescence intensity at 500 nm relative to that at 418 nm, compared to a control or pre-exposure sample.

In an inventive process, the post-exposure photoluminescence is used to determine or measure metal oxyhydroxide contact with an acidic/acid-forming and/or oxidizable gas, and optionally to quantify the amount of an acidic/acid-forming and/or oxidizable gas, that has contacted the metal oxyhydroxide by comparison to a pre-exposure photoluminescence or control. A pre-exposure photoluminescence is measured prior to a metal oxyhydroxide contacting an acidic/acid-forming and/or oxidizable gas using the same techniques of fluorescence spectrometry as are used for measuring a post-exposure photoluminescence. A lower post-exposure ratio of fluorescence intensities indicates that the metal oxyhydroxide has contacted an acidic/acid-forming and/or oxidizable gas. In some embodiments, the post-exposure ratio is compared to a control. A control is a pre-exposure ratio from a similar or identical metal oxyhydroxide. A difference between a post-exposure photoluminescence and a pre-exposure photoluminescence or control allows for the sensing or quantifying contact of a metal oxyhydroxide with an acidic/arid-forming and/or oxidizable gas or other environmental condition.

A process uses one or more metal oxyhydroxides. A metal oxyhydroxide is one or more metal oxides or metal hydroxides that are collectively referred to herein as "metal oxyhydroxide(s)." Illustrative examples of a metal oxyhydroxide include, but are not limited to materials including an alkali or transition metal. More specific examples of a metal oxyhydroxide include but are not limited to zirconium hydroxide, zinc oxyhydroxide, cobalt oxyhydroxide, $Al(OH)_3$, $Mg(OH)_2$, $In(OH)_3$, or combinations thereof. In particular embodiments, a metal oxyhydroxide is an anhydrous zirconium hydroxide ($Zr(OH)_4$). Optionally, a metal oxyhydroxide is not crystalline zirconia ($ZrO_2$).

A metal oxyhydroxide optionally further includes a fluorescent material. A fluorescent material may be, but is not limited to a lanthanide. Compared to organic fluorescent molecules, lanthanides have a longer fluorescent lifetime, they have a large stokes shift such that excitation at a wavelength of 310-350 nm, optionally 340 nm, produces emissions of these molecules in the visible spectrum, and in many instances the FWHM is quite sharp, often of 10 nm or less. These characteristics of fluorescently labeled metal oxyhydroxide improve the sensitivity of the inventive processes. Illustrative examples of fluorescent lanthanides include $Eu^{3+}$, $Tb^{3+}$, $Sm^{3+}$, $La^{3+}$, and $Dy^{3+}$. A metal oxyhydroxide is optionally doped by a fluorescent material by processes known in the art, illustratively by the process described in Bouznit, et al., *Appl. Surf. Sci.*, 2012; 258:2967-2971 or Sun, et al., *J. Materials Chem.*, 2012; 22:8221-8227.

A metal oxyhydroxide may be provided in one or more of many forms. Illustratively, a metal oxyhydroxide may be provided in the form of a powder, granule, particle, or film. A metal oxyhydroxide may be layered within, separate from, or intermixed with a filter material. In some embodiments, a metal oxyhydroxide is placed in close proximity to a filter material, optionally contacting as filter material. Illustrative examples of a filter material include carbon such as ASZM-TEDA carbon. A metal oxyhydroxide may be placed at multiple locations within a bed of filter material such that as an acidic/acid-forming and/or oxidizable gas penetrates the filter material, it also comes into contact with the metal oxyhydroxide so that the metal oxyhydroxide may be used to detect the presence of or amount of an acidic/acid-forming and/or oxidizable gas that the filter material has been exposed to. Such an arrangement may detect a wavefront or exposure front of a gas.

Many different acidic/acid-forming and/or oxidizable gases are detectable by the inventive processes. Illustrative examples include such acidic/acid-forming and/or oxidizable gases as are used for defense or deterrent purposes, or those normally found in a battlefield scenario. Specific illustrative examples include, but are not limited to, sulfur dioxide, nitrogen dioxide, hydrogen chloride, or combinations thereof.

In some embodiments, the inventive processes are capable of detecting exposure of an environmental challenge such as an acidic/acid-forming and/or oxidizable gas that has contacted the metal oxyhydroxide by differing changes in the post-exposure PL ratio relative to a pre-exposure PL ratio or control. Embedding the metal oxyhydroxide in a bed of filtration material uniformly or at one or more discrete locations allows for monitoring bed exposure to an environmental challenge. As one illustrative example, environmental challenge exposure to a first area of a filter bed will red-stretch the photoluminescence of the metal oxyhydroxide at that area while an area of the bed that is more distant from the front face (most exposed) of the filter bed may continue to register unexposed. This would indicate that the filter material has residual life in still being able to perform as expected. Additional exposure to an acidic/acid-forming and/or oxidizable gas as an exemplary environmental challenge, will cause an area of the bed more distal from the front face of the filter material to show a red-stretch indicating additional exposure and less residual life to the filtration media. When an area of the bed shows a red-stretch due to exposure such that an insufficient amount of unexposed filtration media remains, the filter media has reached the end of its useful lifetime. As such, the processes may be used to determine the residual life of the filter material.

As such, processes are provided for determining the residual capacity (lifetime) of an in-service filter or filtration system. Such processes include depositing one or more metal oxyhydroxides within a filter material such as by embedding within one or more portions of filter material, placing the metal oxyhydroxide(s) on a swatch of material, or otherwise locating one or more metal oxyhydroxides within or adjacent to a filter material; contacting an acidic/acid-forming and/or oxidizable gas with the metal oxyhydroxide for a sampling time or contacting said metal hydroxide to heat for a sampling time; obtaining a post-exposure photoluminescence ratio of the metal oxyhydroxide between the photoluminescence at a first wavelength and a second wavelength; and determining said residual capacity by comparing the ratio to a pre-exposure ratio or control.

A metal oxyhydroxide is optionally located in a satellite location to the filter where the satellite location is expected to experience the same challenge by gas, heat or moisture as is to be experienced by a relative filter material. Optionally, a metal oxyhydroxide is located directly adjacent to a filter material. In some embodiments, a metal oxyhydroxide is located at one or several locations embedded within a filter material. Embedding the metal oxyhydroxide in the filter material at various locations allows the monitoring of an exposure front from one surface of a filter to another. As one example presented for illustration only and not as a limitation, a 2 cm thick carbon filter may have two locations of metal oxyhydroxide embedded therein. Exposure to an environmental challenge such as gas, heat or moisture may affect the forward area of the filter material more than the rear area leaving effective filter material present at the rear of the filter. While the environmental challenge will have reduced the residual life of the filter material, the lower exposure of the area near the rear of the filter material will still be functional. Placing metal hydroxides at the various locations allows determination of how much fresh filter material remains.

Alternatively, in some embodiments an environmental challenge will irreversibly or irrevocably alter the filter material such that it is expected that a single exposure will be sufficient to destroy filter effectiveness. The singular detection of exposure by detecting the change in post-exposure photoluminescence of a metal oxyhydroxide relative to pre-exposure photoluminescence or control will indicate that no residual life is present in the filter.

Inventive processes may be performed in situ or ex situ. For ex situ applications, the exposure of a metal oxyhydroxide may occur in a remote location and then transported to a detection location such as a lab (or mobile lab) to determine what chemical contaminants are present and optionally how much exposure the metal oxyhydroxide experienced. For in situ applications, exposure to contaminant gases are optionally measured by a portable fluorometer that may be either separate from or integrated in part or in full within a filter or within the metal oxyhydroxide material itself.

An exemplary instrument useful as a detector for analyzing the photoluminescence of a metal oxyhydroxide is depicted in FIG. 1. A light source 4, is preferably a LED, diode laser, or other portable light source, is configured in electromagnetic contact with as sample 8. The LED is optionally a 335 nm light emitting source. Light from the LED passes through a band pass filter 6 that improves its monochromaticity. The filtered light impinges on a sample bolder 8, optionally a quartz cuvette or quartz tube, that contains the metal oxyhydroxide material. Light emitted at an angle relative, optionally 45 degrees, optionally 90 degrees, to the direction the incident light contacts a beam splitter 10 configured to receive light emitted from the sample and dividing it into two beams. One of these beams impinges on a photomultiplier tube (PMT) module or other suitable detector illustratively a photomultiplier tube (first detector, 12) optionally with a 420 nm bandpass filter in front of it, while the other impinges on a second PMT or other suitable detector illustratively a photomultiplier tube (second detector, 14) optionally with a 500 nm bandpass filter. The purpose of the two detectors with different filters is to determine the intensity of light emitted from the sample at discrete wavelenghts. The entire instrument is powered by and under the control of a power supply and microprocessor 2 configured to control the system and analyze the ratio of the two PMT signals.

The entire detectection system could be miniaturized to fit into a wearable filter or filter system. The detector may be coupled to an alarm or other indicator controlled by the microprocessor to alert a user to the presence of an environmental challenge or to indicate that the filter is in need of replacement.

Also provided are processes of quality control in the manufacture of materials that are or contain one or more metal oxyhydroxides. As the PL spectra of an metal oxyhydroxide is known from the invention, any red-stretch relative to a known standard PL spectra or relative ratio of intensities as is taught herein can indicate poor quality manufacture. As such, an inventive process may include the steps of obtaining a post-manufacture photoluminescence, determining the difference between the post-exposure photoluminescence and a control, and using or rejecting the use of a metal oxyhydroxide material in a filter based on the differnece. If a metal oxyhydroxide material is indistinguishable from the control, the material passes quality inspection and is used for detection of an environmental challenge in a filter. If the metal oxyhydroxide shows a distinguishable ratio relative to control, the material does not pass inspection and is discarded or recycled. The manufacture of the metal oxyhydroxide may be done on site, or at another location and optionally by a vendor. Such processes are optionally used in the manufacture of a filter whereby a metal oxyhydroxide is tested for quality prior to placing in filter.

The proceses of the invention for the first time provide reliable and reproducable detection of an environmental challenge such as the presence of one or more acidic/acid-forming and/or oxidizable gas, heat, or moisture. Rapid determination may be made of the residual life of a filter material to which a metal oxyhydroxide is associated by detection of a shift in the wavelength of light emitted at one or more wavelengths. By detection of a change in the relative intensities at one more wavelengths of the emission spectrum in comparison to a pre-exposure photoluminescence or to a control, a user can quantify the amount of or identify the type of acidic/acid-forming and/or oxidizable gas or other environmental challenge the metal oxyhydroxide has been exposed to.

Various aspects of the present invention are illustrated by the following non-limiting examples. The examples are for illustrative purposes and are not a limitation on any practice of the present invention. It will be understood that variations and modifications can be made without departing from the spirit and scope of the invention. A person of ordinary skill in the art readily understands where any and all necessary reagents or materials may be commercially obtained.

EXAMPLES

Example 1

Detection of Gas Using Metal Oxyhydroxides $Zr(OH)_4$ granules with an average particle size of 7 μm were prepared as described by Peterson, et al., *Ind. Eng. Chem. Res.*, 2009; 48:1694-1698 using powder purchased from Magnesium Elektron, Inc., Manchester, N.J. (product X20631). The powder is used either directly or exposed to water saturated air overnight in a closed vessel to produce hydrated material.

Photoluminescence measurements to determine the effects of gas exposure on the spectrum of $Zr(OH)_4$ are performed either by placing the $Zr(OH)_4$ particles in a U-shaped Schwartz drying tube with glass beads added to increase the surface area and facilitate enhanced contact with flowing gas, or by performing photoluminescence measurements while gases flow over the powder. In the case of ex-situ measurements, the powder is removed from the Schwartz tube following exposure and interrogated by a fluorometer. In the case of in-situ measurements, the powder is placed in a quartz tube in the sample compartment of the fluorometer, and measurements are made during gas exposure. Reactive gases of different concentrations may be delivered by methods known to those skilled in the art including using permeation tubes that emit known quantities at a specific temperature of a chemical of interest and then diluting it with a carrier gas, such as dry air, purified nitrogen, or water-saturated air.

Photoluminescence spectra are acquired using a Fluoro-Max-3 fluorescence spectrometer (Horiba Jobin Yvon, Inc., Edison, N.J.) equipped with a solid sample holder accessory or directly associated with the drying tube. The angle of incidence is optimized for the best signal to noise ratio but held constant for each group of samples. Optical filters were placed in both the excitation and emission paths in order to suppress stray light, to further monochromatize the exciting light and prevent scattered excitation light from entering the detectors. Hoya U340 and Schott GG385 filters are used in the excitation and emission paths, respectively. The excitation wavelength is 340 nm.

Figure 2:
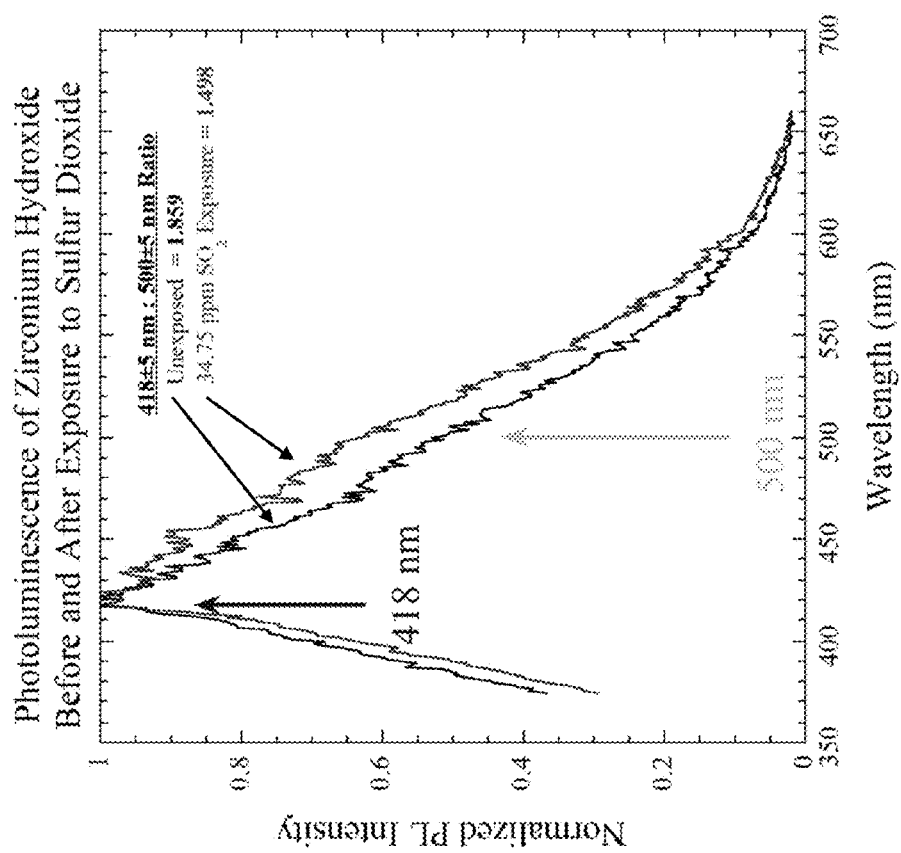
FIG. 2 illustrates an in situ photoluminescence measurement peak shape change or "stretch" toward longer wavelengths in which granulated zirconium hydroxide was exposed to 35 ppm of sulfur dioxide.

FIG. 2 illustrates a red-stretch of emitted light following exposure to 34.75 ppm $SO_2$. The normalized signal intensities reveal a photoluminescence ratio at 418 nm to 500 nm that is significantly decreased illustrating a red-stretch of the emission spectrum and demonstrating reaction of the $SO_2$ with the $Zr(OH)_4$ granules. Similar experiments are run using either purified $N_2$, 7.73 ppm $SO_2$, 4.85 ppm $NO_2$, or 1% HCl in purified $N_2$. The presence of the gas significantly and specifically alters the 418 nm:500 nm photoluminescence ratio with the $NO_2$ demonstrating the greatest red-stretch.

Figure 3:
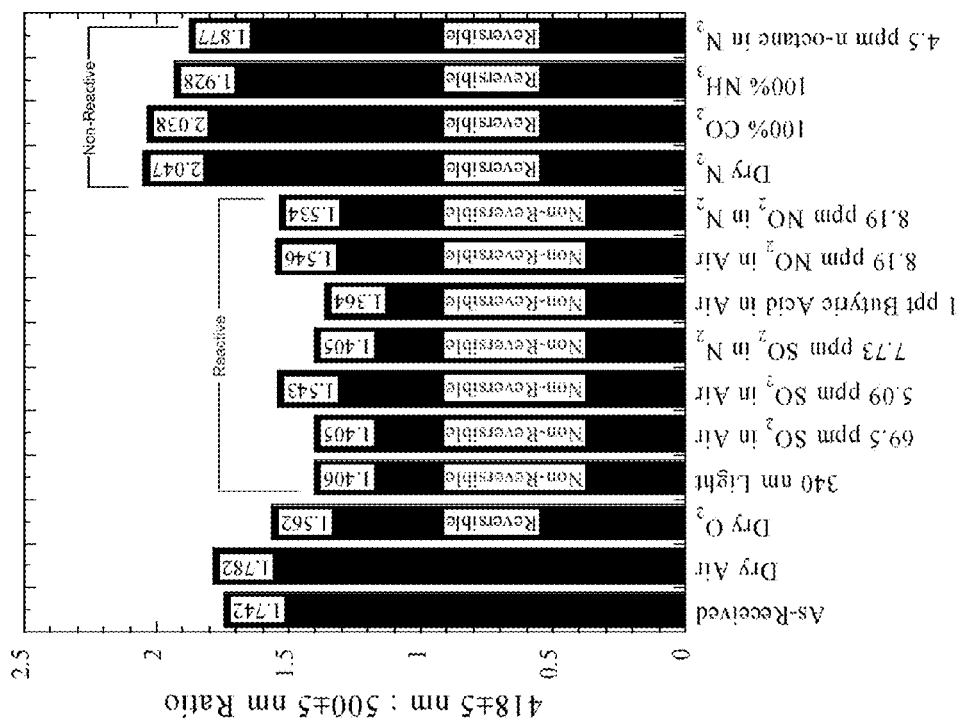
FIG. 3 illustrates a summary of the ratio of the 418 nm to 500 nm intensities in the photoluminescence spectrum of granulated zirconium hydroxide following exposure to sulfur dioxide, nitrogen dioxide, ammonia, butyric acid, and n-octane in various carrier gasses.

Additional tests are performed using the $Zr(OH)_4$ granules with various carrier gases either pre-exposure to the environmental gas, or following exposure to the environmental gas with results depicted in FIG. 3. $Zr(OH)_4$ granules as received from the vendor show a photoluminescence ratio of 1.742. Purging the granules with dry air increases the ratio somewhat. Purging the granules with dry purified $O_2$ reduces the ratio somewhat. Flowing sulfur dioxide or nitrogen dioxide through the granules allows the gas to react with free terminal hydroxyl groups on the $Zr(OH)_4$ material. This results in an irreversible reaction that allows subsequent analysis of prior exposure. The presence of either $SO_2$ or $NO_2$ gas red-stretches the spectrum reducing the photoluminescence ratio significantly. Exposure of the granules to 69.5 ppm $SO_2$ in air shows a ratio reduction of greater than 0.3. The granules can detect and distinguish various concentrations of $SO_2$ as illustrated by the presence of 5.09 ppm $SO_2$ demonstrating nearly a 0.15 increase in ratio. Thus, the higher ratio indicates lower exposure. Similar results are observed for $NO_2$ gas. Butyric acid gas at 1 ppt (parts per thousand) in air is also tested. A significant decrease in ratio is observed relative to pre-exposure in air alone indicating that butyric acid gas exposure can also be detected by the system.

Carrier gas alone is non-reactive with the granules showing no red stretch following sample exposure. Similarly, n-octane and ammonia (data not shown) gases in purified nitrogen at 4.5 ppm are non-reactive. Overall, these results demonstrate the ability to detect exposure to $SO_2$ or $NO_2$ gases and quantify the amount of exposure useful in systems as detection for end of life indicator or other use.

Example 2

Detection Heat Exposure Using Metal Oxyhydoxide

Figure 4:
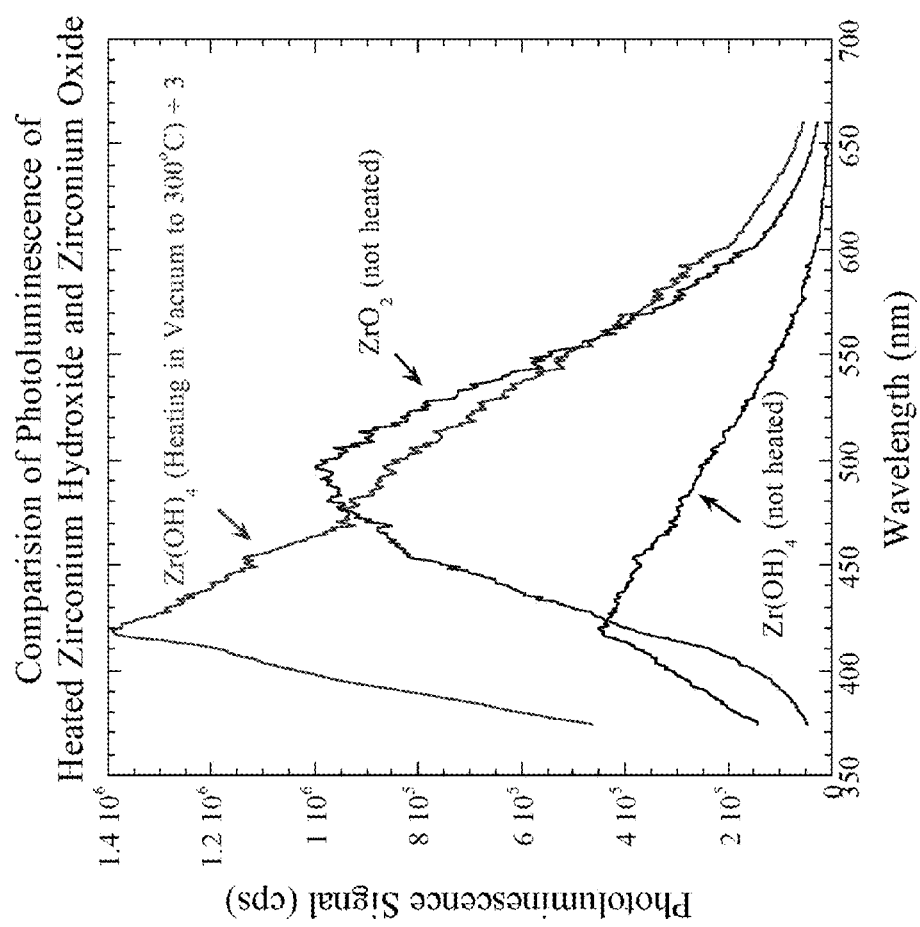
FIG. 4 illustrates an in situ photoluminescence shape change or stretch produced in granulated zirconium hydroxide by exposure to heat of 300° C.
Figure 5B:
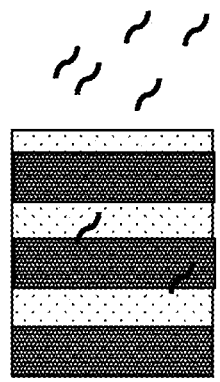
FIG. 5(b) illustrates a packed bed of filter material associated with metal oxyhydroxide located at discrete locations within the filter bed where ↙ denotes an environmental challenge.
Figure 5C:
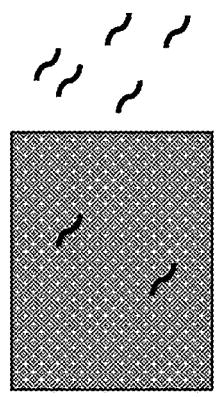
FIG. 5(c) illustrates a packed bed of filter material associated with a metal oxyhydroxide embedded entierly within the bed of filter material where ↙ denotes an environmental challenge.
Figure 5A:
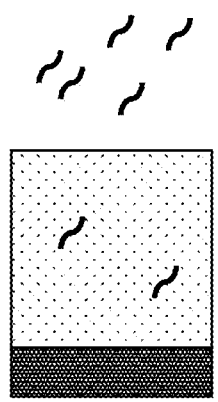
FIG. 5(a) illustrates a packed bed of filter material associated with a metal oxyhydroxide located at an end of the filter bed distal from an exposure surface where ↙ denotes an environmental challenge.

The $Zr(OH)_4$ granules prepared as in Example 1 are subjected to heat as an environmental stress. The granules are heated at 300° C. in a vacuum for 2 hours. The material is then assayed for photoluminescence properties as in Example 1. The results are depicted in FIG. 4. Exposure of the granules to heat causes a significant red stretch in the emission spectrum, with greater relative intensity at longer wavelengths. The red-stretch value for $Zr(OH)_4$ heated to 300° C. is 1.5. For $ZrO_2$, it is 0.2-0.3.

It is appreciated that all reagents are obtainable by sources known in the art unless otherwise specified.

REFERENCES

[1] Peterson, G. W.; Karwacki, C. J.; Feaver, W. B.; Rossin, J. A. "Zirconium Hydroxide as a Reactive Substrate for the Removal of Sulfur Dioxide." *Ind. Eng. Chem. Res.* 2009, 48, 1694-1698.

[2] Peterson, G. W.; Wagner, G. W.; Keller, J. H.; Rossin, J. A. "Enhanced Cyanogen Chloride Removal by the Reactive Zirconium Hydroxide Substrate." *Ind. Eng. Chem. Res.* 2010, 49, 11182-11187.

[3] Peterson, G. W. and Rossin, J. A. "Removal of Chlorine Gases from Streams of Air Using Reactive Zirconium Hydroxide Based Filtration Media." *Ind. Eng. Chem. Res.* 2012, 51, 2675-2681.

[4] Bandosz, T. J.; Laskoski, M.; Mahle, J.; Mogilevsky, G.; Peterson. G. W.; Rossin, J. A.; Wagner, G. W. "Reactions of VX, GD, and HD with $Zr(OH)_4$: Near Instantaneous Decontamination of VX." *J. Phys. Chem. C* 2012, 116, 11606-11614.

[5] Rossin, J. A.; Peterson, G. W.; Feaver, W.; Karwacki, C. J. U.S. patent application Ser. No. 12/914,134, Filed Oct. 28, 2010.

[6] Singh, J.; Mukherjee, A.; Sengupta, S. K.; Im, J.; Peterson, G. W.; Whitten, J. E. Sulfur dioxide and nitrogen dioxide adsorption on zinc oxide and zirconium hydroxide nanoparticles and the effect on photoluminescence. *Applied Surface Science* 2012, 258, 5778-5785.

[7] Peterson, G. W.; Karwacki, C. J.; Friday, D.; Shrewsbury, M. U.S. Pat. No. 8,205,483, Jun. 26, 2012.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A process for sensing an acidic/acid-forming and/or oxidizable gas, comprising:
   calculating a control or pre-exposure ratio of photoluminescence intensity at a first wavelength and a second wavelength for a metal oxyhydroxide;
   contacting an acidic/acid-forming and/or oxidizable gas with said metal oxyhydroxide for a sampling time;
   calculating a post-exposure ratio of photoluminescence intensity at said first wavelength and said second wavelength for said metal oxyhydroxide;
   determining a difference between said post-exposure ratio of photoluminescence and a said pre-exposure ratio of photoluminescence or control; and
   sensing said acidic/acid-forming and/or oxidizable gas by said difference.

2. The process of claim 1, wherein said acidic/acid-forming and/or oxidizable gas directly reacts with a surface of said metal oxyhydroxide.

3. The process of claim 1, wherein said acidic/acid forming gas is sulfur dioxide, nitrogen dioxide, hydrogen chloride, or combinations thereof.

4. The process of claim 1, wherein said metal oxyhydroxide comprises an alkali or transition metal.

5. The process of claim 1, wherein said metal oxyhydroxide is zirconium hydroxide, zinc oxyhydroxide, cobalt oxyhydroxide, or combinations thereof.

6. The process of claim 1, wherein said metal oxyhydroxide further comprises one or more fluorescent materials doped in said metal oxyhydroxide.

7. The process of claim 6, wherein said fluorescent material is a lanthanide.

8. The process of claim 1, wherein said post-exposure photoluminescence is a ratio of intensity of a first wavelength and a second wavelength.

9. The process of claim 8, wherein said first wavelength is 418 nanometers and said second wavelength is 500 nanometers.

10. The process of claim 1, wherein said metal oxyhydroxide is amorphous zirconium hydroxide.

11. A process for determining residual capacity of an in-service filter/filtration system, comprising:
    depositing one or more metal oxyhydroxides on a swatch of material or locating one or more metal oxyhydroxides within a filter material;
    a) contacting an acidic/acid-forming and/or oxidizable gas with said metal oxyhydroxide for a sampling time; or
    b) contacting said metal hydroxide to heat for a sampling time;
    obtaining a post-exposure photoluminescence ratio of said metal oxyhydroxide between the photoluminescence at a first wavelength and a second wavelength;
    and determining said residual capacity by comparing said ratio to a pre-exposure ratio or control.

12. The process from claim 11, wherein said metal oxyhydroxide comprises an alkali or transition metal.

13. The process of claim 11, wherein said metal oxyhydroxide is amorphous zirconium hydroxide, zinc oxyhydroxide, cobalt oxyhydroxide, or combinations thereof.

14. The process of claim 11, wherein said step of locating is by locating said metal oxyhydroxide in said filter material so as to be capable of tracking a wavefront of said acidic/acid-forming or oxidizable gas through said filter.

15. The process of claim 11, wherein said metal oxyhydroxide is located in said filter distal from an exposure surface of said filter material.

16. The process of claim 11, further comprising integrating a detector or portion thereof within said filter in electromagnetic contact with said metal oxyhydroxide.

17. The process from claim 11, wherein said metal oxyhydroxide further comprises one or more fluorescent materials doped in said metal oxyhydroxide.

18. The process of claim 17, wherein said fluorescent material is a lanthanide.

19. A process for manufacture of a metal oxyhydroxide material, comprising:
    obtaining a post-manufacture ratio of photoluminescence at a first wavelength and a second wavelength of a metal oxyhydroxide material;
    determining a difference between said post-manufacture ratio of photoluminescence and a control; and
    using or rejecting the use of a metal oxyhydroxide material based on said difference.

20. The process of claim 19, further comprising assembling a filter media, filter housing, or filtration system including the metal oxyhydroxide.

21. The process from claim 19, wherein said metal oxyhydroxide comprises an alkali or transition metal.

22. The process from claim 19, wherein said metal oxyhydroxide is zirconium hydroxide, zinc oxyhydroxide, cobalt oxyhydroxide, or combinations thereof.

23. The process from claim 19, wherein said metal oxyhydroxide further comprises one or more fluorescent materials doped in said metal oxyhydroxide.

24. The process of claim 23, wherein said fluorescent material is a lanthanide.

25. The process of claim 1, wherein said sensing is based upon said post-exposure photoluminescence ratio being a lower ratio than said pre-exposure photoluminescence ratio.

26. The process of claim 1, wherein said first wavelength is 418 nanometers and said second wavelength is 500 nanometers.

* * * * *